(12) United States Patent
Johnson

(10) Patent No.: US 6,255,117 B1
(45) Date of Patent: Jul. 3, 2001

(54) METHOD AND DEVICE FOR DETERMINING MONOPERSULFATE

(75) Inventor: Lydia Johnson, Denton, MD (US)

(73) Assignee: Lamotte Company, Chestertown, MD (US)

( * ) Notice: Subject to any disclaimer, the term of this patent is extended or adjusted under 35 U.S.C. 154(b) by 0 days.

(21) Appl. No.: 09/325,792

(22) Filed: Jun. 4, 1999

(51) Int. Cl.$^7$ .................................................. G01N 33/00
(52) U.S. Cl. .......................... 436/119; 436/120; 436/123; 436/125; 436/169; 436/164; 436/810; 436/815; 436/904; 422/56; 435/4; 435/805; 427/2.13
(58) Field of Search .................................. 436/119, 120, 436/123, 125, 169, 164, 810, 815, 904; 422/56; 435/4, 805; 427/2.13

(56) References Cited

U.S. PATENT DOCUMENTS

| | | | |
|---|---|---|---|
| 4,092,115 | 5/1978 | Rupe et al. | 23/230 R |
| 4,393,142 | * 7/1983 | Stephens | 436/125 |
| 4,904,605 | * 2/1990 | O'Brien et al. | 436/169 |
| 5,491,094 | * 2/1996 | Ramana et al. | 436/125 |
| 5,811,254 | 9/1998 | Wu | 435/28 |
| 5,972,713 | * 10/1999 | Kuzuhara et al. | 436/125 |
| 5,976,823 | * 11/1999 | Wu | 435/28 |
| 6,028,045 | * 2/2000 | Bianchetti et al. | 510/309 |
| 6,030,842 | * 2/2000 | Peachey-Stoner | 436/125 |
| 6,087,089 | * 7/2000 | Wu | 435/4 |
| 6,180,412 | * 1/2001 | Kroll | 436/125 |

OTHER PUBLICATIONS

J. Liebermann, Jr. et al., "Development of the FACTS Procedure for Combined Forms of Chlorine and Ozone in Aqueous Solutions," Environ. Sci. Technol., 14, 11, 1395–1400 (1980).

* cited by examiner

Primary Examiner—Jill Warden
Assistant Examiner—Monique T. Cole
(74) Attorney, Agent, or Firm—Gipple & Hale

(57) ABSTRACT

A test method and device are described for quantitatively determining the presence and concentration of monopersulfate ion in aqueous solution. Contacting the aqueous solution containing monopersulfate ion with a test strip in accordance with the invention produces a color change in proportion to the concentration of the ion. The invention has particular utility in maintaining the proper level of sanitizers in swimming pool water.

12 Claims, No Drawings

METHOD AND DEVICE FOR DETERMINING MONOPERSULFATE

FIELD OF THE INVENTION

The present invention is directed to a device and method for determining the concentration of monopersulfate salts or ions in aqueous solutions.

BACKGROUND OF THE INVENTION

Monopersulfate salts, such as potassium monopersulfate, are useful as oxidants in many applications including swimming pool treatment denture cleaning and paper recycling. Although monopersulfate salts (MPS) are not sanitizers and cannot be used alone in pools and spas, they are used as auxiliary oxidants (shocking agent) in conjunction with copper/silver ionizers or chlorine or bromine sanitizers to reduce organic content in swimming pool or spa water. In this manner MPS improves the sanitizer's efficiency and the aesthetic quality of the pool water.

Shocking can be defined as a pool or spa water treatment that oxidizes chloramines and other organic contaminants making pool and spa water clear. Many organic contaminants, such as perspiration, body oils, deodorants, and suntan lotions are introduced into pool and spa water by the bather. Other contaminants are introduced by external forces, such as wind and rain; these include dust and dirt, pollen and other plant debris, lawn fertilizer, grass clippings, and airborne pollutants.

It is widely known and accepted that proper sanitation is critical for maintaining pool and spa water free of disease and infection causing bacteria, viruses, and other microorganisms. When organic contaminants build up, they chemically react with swimming pool sanitizing and disinfecting chemicals, consuming a large portion of the available sanitizer. As this occurs, the sanitizer must be added at higher doses to achieve the same level of disinfection. As the level of organic contaminants increases in pool and spa water, the sanitizer concentration and disinfection efficiency decreases.

Contaminants which contain nitrogen, such as ammonia, can combine with chlorine sanitizers to form chloramines, or combined chlorines. There are many problems associated with the presence of combined chlorines. They react with active chlorine, they irritate eyes and mucous membranes, they create chlorine-like odors, and they are poor sanitizers.

In addition to reducing sanitizer efficiency and generating irritating and odorous chloramines, organic contaminants also adversely affect the aesthetic quality of swimming pool and spa water. They make the water appear dull, thick, slow, and cloudy.

Monopersulfate shocking eliminates organic contaminants, increases sanitizer efficiency, and restores sparkle and clarity to pool and spa water.

While monopersulfate are, accordingly, useful either as alternative or in addition to other water treatments such as chlorine shocking, it is important to be able to quickly and effectively determine the concentration of monopersulfate in the aqueous medium if the treatment is to be safe and effective.

SUMMARY OF THE INVENTION

In accordance with the present invention, a composition, method and device are provided for determining the concentration of monopersulfate ions in aqueous solution. The device of the invention includes an absorbent matrix, such as cellulose based paper, onto which the indicator reagent composition is absorbed and then dried to form a test strip. The composition of the invention is capable of reacting with monopersulfate in aqueous solution at concentrations from 0–50 ppm to give a color change indicative of the concentration of monopersulfate present.

The method of the invention comprises contacting a test solution with the composition of the invention, which may be a dried deposit on an absorbent matrix, observing the resultant color change and comparing the resultant color with a standard color index of colors at specific monopersulfate concentrations to quantitatively determine the monopersulfate concentration.

DETAILED DESCRIPTION OF THE INVENTION

The composition, method and device of the present invention for measuring the monopersulfate ion concentration in aqueous solutions includes an indicator reagent composition deposited on a carrier matrix of suitable bibulous material such as a cellulosic matrix and capable of reacting with monopersulfate ions to form iodine and reacting with the iodine to give a color change in proportion to the concentration of monopersulfate ion present over a range of 0–50 ppm. The indicator composition comprises:

Redox indicator that gives a color change on reaction with iodine, such as heterocyclic azine and benzidine type indicators A buffer for buffering the composition in the pH range 5–7, such as an alkalic metal phosphate 0.1–2% of a cationic surfactant 0.1–2% of a polymer to increase solubility and compatibility Source, such as potassium or sodium iodide, which on reaction with monopersulfate ions forms Iodine A suitable carrier matrix of bibulous material either natural or synthetic such as absorbent paper.

Typical redox indicators for the invention are compounds of the formula:

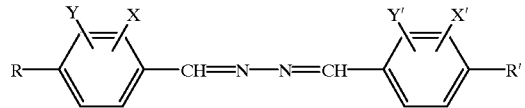

where R and R' are selected from the group consisting of hydroxy and amino groups and X,X',Y and Y' are selected from the group consisting of hydrogen, hydroxy, methyl, methoxy, ethyl and ethoxy groups

EXAMPLE I

The test device of the invention was prepared as follows:

Dipping solution A—Potassium buffer, pH 5.75 with 0.01% KI

Dipping solution B—0.1% syringealdezine in methyl ethyl ketone

Whatman 3MM paper was immersed in A and then dried for 20 minutes in forced air oven at 60 C. The dried paper was re-immersed in Solution B and dried 25 minutes in a forced air oven at 4 0C.

The strips were swirled in MPS samples of known concentration 5 times. After 30 seconds the results were read as follows:

| concentration | |
|---|---|
| MPS | Reaction color |
| 0ppm | white |
| 5 | trace |
| 15 | lavender |
| 50 | dark lavender |

EXAMPLE II

Example 1 was repeated with variations in the potassium iodide concentration as follows:

| | Monopersulfate concentration | | | |
|---|---|---|---|---|
| KI | 0ppm | 5 ppm | 15 ppm | 50 ppm |
| 0.001% | white | white | white | trace |
| 0.005% | white | white | trace | lavender |
| 0.01% | white | trace | lavender | dark lavender |
| 0.05% | white | pale lavender | lavender | dark lavender |
| 0.1% | white | trace | trace | pale lavender |
| 0.5% | white | trace | very pale | pale lavender |

EXAMPLE III

| | Monopersulfate concentration | | | |
|---|---|---|---|---|
Example 1 was repeated with variations in the pH of the phosphate buffer:

| pH | 0ppm | 5 ppm | 15 ppm | 50 ppm |
|---|---|---|---|---|
| 3 | pale yellow | pale yellow | pale yellow | pale yellow |
| 4.5 | white | white | trace | pale lavender |
| 5 | white | white | trace | pale lavender |
| 5.5 | white | trace | pale lavender | lavender |
| 5.75 | white | trace | lavender | dark lavender |
| 6.5 | white | trace | lavender | dark lavender |
| 7 | white | trace | pale lavender | lavender |
| 7.5 | pale yellow | pale orange | pale peach/purple | dark lavender |
| 8 | pale yellow | trace | peach | peach |

While a preferred embodiment of the instant invention has been herein described, it will be understood that other embodiments and alternatives are considered to fall within the scope of the invention as defined in the claims. It will, for example, be appreciated by those of ordinary skill in the art that various colorgraphic and chromagraphic procedures can be employed to quantify color changes in the test device and composition. It will also be understood that various alternative buffers, solubilizers, color intensifiers, surfactants and indicators can be employed without departing from the intended scope of the invention

What is claimed is:
1. A method for the determination of monopersulfate salts in aqueous solutions comprising:
A. Contacting a test solution sample with a reagent composition comprising:
a) a chromatic indicator capable of reacting with iodine to give a color change;
b) a buffer to maintain the test solution and composition at a pH of 5 to 7;
c) 0.01 to 0.05% iodide salt;
d) 0.1 to 2.0 cationic surfactant;
e) 0.1 to 2.0% of a solubilizing polymer;
B. Comparing the color responses obtained to color responses from standardized solutions of monopersulfate salts and translating such comparisons to the amount of monopersulfate salt in the test solution.
2. The method of claim 1 wherein said chromatic indicator material is a heterocyclic azine or benzidine.
3. The method of claim 1 wherein said iodide salt is potassium iodide or sodium iodide.
4. The method of claim 1 wherein the reagent composition is incorporated onto a fluid absorbent matrix material and the matrix is contacted with the test solution sample.
5. The method of claim 4 wherein the fluid absorbent matrix material is a cellulose based paper.
6. The method of claim 2 wherein said indicator is syringalidazine.
7. A method for the determination of monopersulfate salts in aqueous solutions comprising: A. contacting a test solution sample with a reagent composition deposited on an absorbent matrix material comprising a) a chromogenic indicator material selected from the group consisting of (1) a compound having the formula

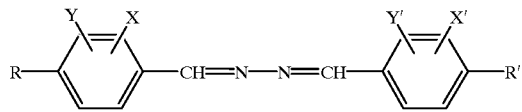

where R and R' are selected from the group consisting of hydroxy and amino groups and X,X',Y and Y' are selected from the group consisting of hydrogen, hydroxy, methyl, methoxy, ethyl and ethoxy groups; b) a buffer to maintain the test composition and test solution sample in a pH range of about from 5 to 7; c) 0.01 to 0.05 % iodide salt; d) 0.5 to 1.5% cationic surfactant and; e) 4 to 6% polymeric bonding agent, and B. comparing the color response obtained to color responses from standardized solutions of monopersulfate salts and translating such comparison to the amount of monopersulfate salt in the test solution.
8. A test device for the determination of monopersulfate salts in aqueous s solutions comprising a matrix material incorporated with the dried residue of a test composition comprising:
a) a chromatic indicator capable of reacting with iodine to give a color change;
b) a buffer to maintain the test solution and composition at pH of 5 to 7;
c) 0.01 to 0.05% iodide salt
d) 0.1 to 2.0% cationic surfactant
e) 0.1 to 2.0% of a solubilizing polymer.
9. The test device of claim 8 wherein said chromogenic indicator is a heterocyclic azine or benzidine.
10. The test device of claim 9 wherein said chromogenic indicator is syringaldazine.
11. The test device of claim 10 wherein said iodide salt is potassium iodide or sodium iodide.
12. The test device of claim 10 wherein said matrix material is absorbent cellulosic material is paper.

* * * * *